United States Patent [19]

Mayer et al.

[11] Patent Number: 5,130,428

[45] Date of Patent: Jul. 14, 1992

[54] PREPARATION OF 6-TRIFLUOROMETHYL-1,3,5-TRIAZINES

[75] Inventors: Horst Mayer, Ludwigshafen; Gerhard Hamprecht, Weinheim, both of Fed. Rep. of Germany

[73] Assignee: BASF Aktiengesellschaft, Ludwigshafen, Fed. Rep. of Germany

[21] Appl. No.: 769,839

[22] Filed: Oct. 2, 1991

[30] Foreign Application Priority Data

Oct. 26, 1990 [DE] Fed. Rep. of Germany ....... 4034078

[51] Int. Cl.$^5$ .......................................... C07D 251/42
[52] U.S. Cl. ...................................... 544/194; 544/213
[58] Field of Search ............................... 544/194, 213

[56] References Cited

FOREIGN PATENT DOCUMENTS 252374 12/1987 Fed. Rep. of Germany .

OTHER PUBLICATIONS

Patent Abstracts of Japan 5 1068-581, Jun. 14, 1976 and Japan Application No. 141726, Dec. 10, 1974.
Patent Abstract of Japan 5 2025-785, Feb. 25, 1977 and Japan Application No. 100447, Aug. 19, 1975.
Patent Abstract of Japan 5 2083-577, Jul. 12, 1977 and Japan Application No. 000215, Jan. 1, 1976.
Patent Abstract of Japan 5 2025-786, Feb. 25, 1977, and Japan Application No. 101967, Aug. 22, 1975.
Patent Abstract of Japan 5 2083-576, Jul. 12, 1977, and Japan Application No. 000211, Jan. 1, 1976.
Patent Abstract of Japan 5 2083-582, Jul. 12, 1977, and Japan Application No. 000216, Jan. 1, 1976.
Canadian Journal of Chemistry, vol. 35, (1957), "The reaction of acetic and trifluoroacetic anhydrides with some substituted Guanidine Hydrochlorides", W. F. Cockburn, et al., pp. 1285-1292.
Z. Anorg. Allg. Chem. 589 (1990) 69-78, S. Lotz and G. Gattow, "Acetylation Reactions" pp. 69-78, with translation.
"Syntheses and Reactions of 2-Halo-5-thiazolecarboxylates", Len F. Lee, et al., J. Heterocyclic Chem. 22, Nov.-Dec. 1985, pp. 1621-1630.

Primary Examiner—John M. Ford
Attorney, Agent, or Firm—Oblon, Spivak, McClelland, Maier & Neustadt

[57] ABSTRACT

6-Trifluoromethyl-1,3,5-triazines I

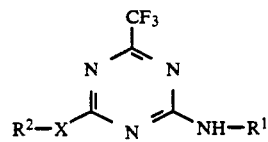

(X=O,S; R$^1$=H; R$^1$, R$^2$=carbon organic radicals) are prepared by reacting
(a) N-trichloroacetamidinoguanidines II

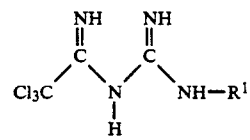

with trifluoroacetic acid derivatives III

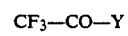

(Y=Cl, alkoxy, CF$_3$—CO—O) to give 4-trichloromethyl-6-trifluoromethyl-1,3,5-triazines IV

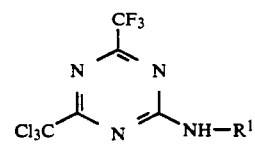

and
(b) reacting the products IV in the presence of a base with alcohols V

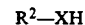

The triazines I are valuable intermediates for crop protection agents.

7 Claims, No Drawings

PREPARATION OF 6-TRIFLUOROMETHYL-1,3,5-TRIAZINES

The present invention relates to a novel process for preparing 6-trifluoromethyl-1,3,5-triazines of the formula I

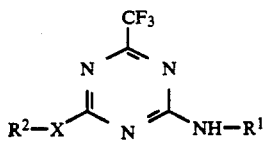

where X is oxygen or sulfur, $R^1$ and $R^2$ are each carbon organic substituents with 1 to 6 carbons and $R^1$ is additionally hydrogen.

JP-A 52 025786, JP-A 52 025785 and JP-A 52 083577 disclose the conversion of N-trichloroacetamidinotrichloroacetamidine into 2,4-bis-trichloromethyl-6-trifluoromethyl-1,3,5-triazine with 2.2 mole equivalents of trifluoroacetic anhydride as shown in the following diagram

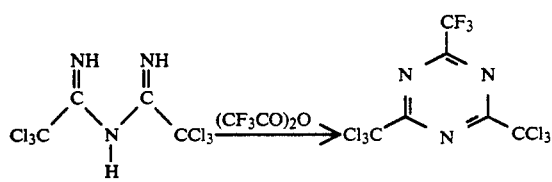

Formal replacement of one of the two electron-attracting trichloromethyl groups in the N-trichloroacetamidinotrichloroacetamidine by an electron-repelling amino group results in the trichloroacetamidinoguanidines II. In this case it ought accordingly to be easier for there to be attack by strong electrophiles such as trifluoroacetic anhydride or trifluoroacetyl chloride than in the case of the comparatively electron-depleted amidines.

Z. anorg. allg. Chem. 589 (1990) 69-78 discloses that reaction of N-(trichloromethylcarbimidoyl) guanidine with acetic anhydride gives heteroaromatic 1,3,5-triazine systems. By contrast, attempts at acetylation with ethyl acetate under a wide variety of conditions revealed no evidence of a chemical reaction.

According to Can. J. Chem. 35 (1957) 1285, guanidines are converted by reaction with acetic anhydride or, in particular, trifluoroacetic anhydride into diacylated derivatives which can, in certain cases, be cyclized to triazines:

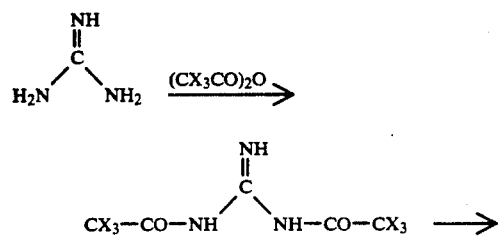

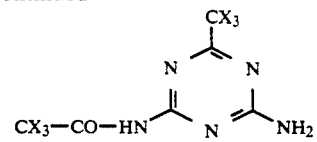

X=H, F.

The final cyclization step is, however, not possible either with the hydrochloride of guanidine or with that of cyclohexylguanidine when trifluoroacetic anhydride is used as electrophile, so that in these cases only the diacylguanidines (X=F) are obtained as products.

Accordingly, reaction of the N-trichloroacetamidinoguanidines II with trifluoroacetic anhydride or trifluoroacetyl chloride would be expected to result in bisacylation of the guanidine moiety without subsequent cyclization of the diacylated products:

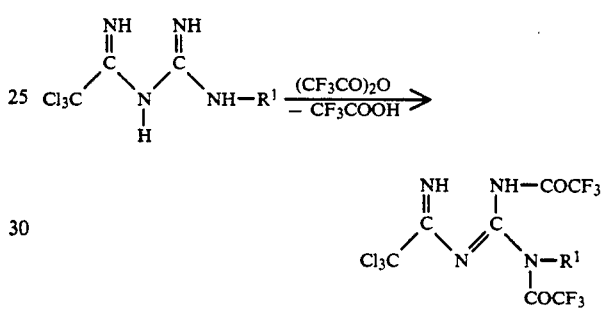

However, JP-A 51 068 581, JP-A 52 025 786, JP-A 52 083 576 and JP-A 52 083 582 disclose that it is possible to prepare the 2-amino-4-trichloromethyl-6-trifluoromethyl-1,3,5-triazines IV from the abovementioned 2,4-bis-trichloromethyltriazines by replacing a trichloromethyl group by anamino radical. This 2-stage process has, however, the industrially unsatisfactory aspect that chloroform is produced in equimolar amounts as by-product. In addition, a simpler synthesis with only one step would be desirable.

The comparable replacement of the remaining trichloromethyl group in the compound IV by alkoxy is expected to be in competition with the replacement of the three fluorine atoms with the formation of an orthoester (Williamson reaction; cf. R. H. de Wolfe in Carboxylic Ortho Acid Derivatives, Acad. Press., New York, 1970, pates 12 to 18). It is disclosed, in particular, in J. Heterocycl. Chem. 22 (1985) 1621 that the trifluoromethyl group on a thiazole structure is converted even under mild conditions into an orthoester:

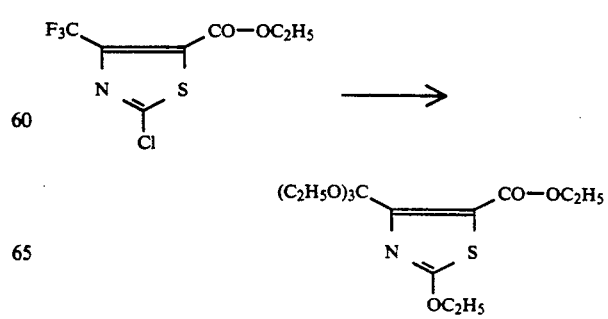

Another possibility for the preparation of 6-trifluoromethyl-1,3,5-triazines is a process disclosed in Yakugaku Zasshi 95 (1975) 499–511 in which N-cyanoguanidines are converted into copper complexes of N-amidino-O-alkylisoureas, and the urea derivatives are liberated with hydrogen sulfide and then reacted with trifluoroacetic ester as shown in the following diagram

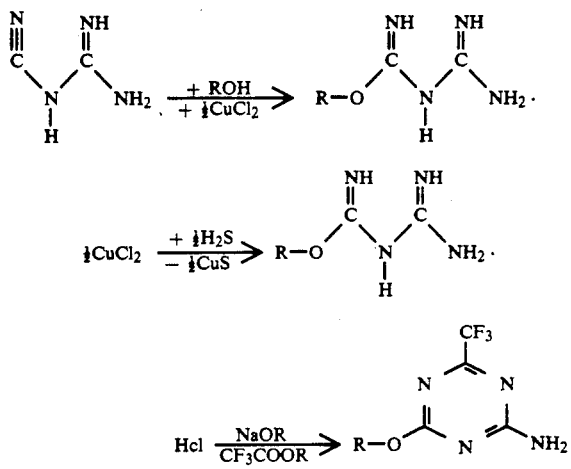

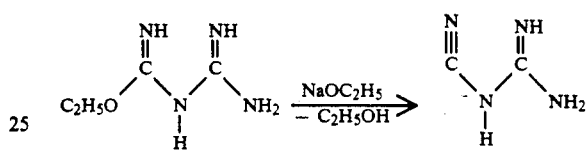

DD-A 252 374 discloses a variant of this process in which the copper (II) chloride is replaced by copper acetate, and the copper complex of N-amidino-O-alkylisourea formed in the first step is reacted immediately with trifluoroacetic anhydride to give a 6-trifluoromethyl-1,3,5-triazine.

However, a great disadvantage of both processes is that the preparation of the N-amidino-O-alkylisoureas entails the necessity to remove and dispose of large amounts of copper salts as by-product, which makes implementation on the industrial scale appear uneconomic.

Other syntheses of 6-trifluoromethyl-1,3,5-triazines starting from N-amidino-O-alkylisoureas are disclosed, for example, in DE-A 1 220 431, DE-A 3 324 800, EP-A 98 569, FR-A 11 380 818, U.S. Pat. No. 3 258 462, Chem. Pharm. Bull. 16 (1968) 474 and 21 (1973) 478. However, the disadvantage of these reactions is the sensitivity, disclosed in Chem. Pharm. Bull. 16 (1968) - 474, of N-amidino-O-alkylisoureas to bases such as sodium ethanolate, there being formation of cyanoguanidines:

Since the trichloromethyl group of the N-trichloroacetamidinoguanidines II is likewise a good leaving group like the alkoxy group of the N-amidino-O-alkylisoureas, the sensitivity of compounds II to bases ought to be comparable:

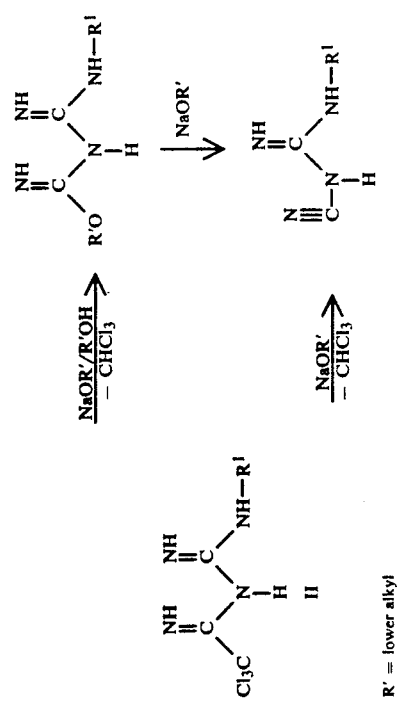

R'=lower alkyl

To avoid such decompositions, the cited literature makes use either of no base or, to liberate the N-amidino-O-alkylisoureas from their salts, equimolar amounts of base or a small excess of up to about 10 mol %. Nevertheless, only very unsatisfactory yields of the required triazines are obtained, especially in the presence of larger amounts of base.

It is an object of the present invention to make the compounds I more easily accessible.

We have found that this object is achieved by a process for preparing 6-trifluoromethyl-1,3,5-triazines of the formula I, which comprises (a) reacting an N-trichloroacetamidinoguanidine of the formula II

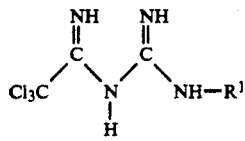

with a trifluoroacetic acid derivative of the formula III

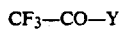

CF$_3$—CO—Y     III where Y is chlorine, C$_1$–C$_4$-alkoxy or trifluoroacetoxy, in the presence or absence of a base to give a 4-trichloromethyl-6-trifluoromethyl-1,3,5-triazine of the formula IV

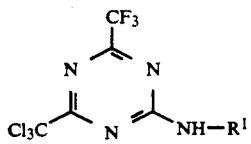

and (b) reacting the product IV in the presence of a base with an alcohol or thiol of the formula V

R$^2$—XH     V

The N-trichloroacetamidinoguanidines II used as starting materials are disclosed in Rec. Trav. chim. 70 (1951) 638 [CA 1952, 8610d] or can be prepared by the method described therein from trichloroacetonitrile and an N-substituted guanidine as shown in the diagram below

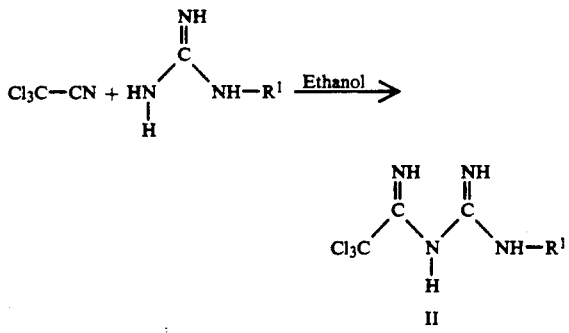

The guanidine can also be employed in the form of an acid addition salt, in which case the acid liberated during the reaction is expediently neutralized by adding a suitable base such as sodium ethanolate.

Carbon organic radicals for R$^1$ in formula I are, in particular, aliphatic, cycloaliphatic or aromatic radicals, e.g. lower alkyl, alkenyl, alkynyl or cycloalkyl, R$^2$ can be, for example, an aliphatic or cycloaliphatic radical such as lower alkyl, alkenyl or alkynyl.

In view of the use of the intermediates I to be prepared, the starting compounds II are preferably those where R$^1$ is hydrogen, C$_1$–C$_4$-alkyl such as methyl, ethyl, n-propyl, isopropyl, n-butyl, sec-butyl or tert-butyl, C$_3$–C$_6$-cycloalkyl such as cyclopropyl, cyclopentyl or cyclohexyl, or phenyl. Particularly preferred radicals are hydrogen or C$_1$–C$_4$-alkyl.

R$^2$ in the compounds to be prepared according to the invention is preferably

C$_1$–C$_4$-alkyl such as methyl, ethyl, n-propyl, isopropyl, n-butyl, sec-butyl and tert-butyl;

C$_3$–C$_4$-alkenyl such as 2-propenyl, 1-methyl-2-propenyl, 2-butenyl and 3-butenyl;

C$_3$–C$_4$-aklynyl such as 2-propynyl and 2-butynyl;

C$_3$–C$_6$-cycloalkyl such as cyclopropyl, cyclobutyl, cyclopentyl and cyclohexyl, preferably cyclopentyl and cyclohexyl.

R$^2$ can in turn carry further substituents (which are inert in step (b)).

Suitable trifluoroacetic acid derivatives III are principally trifluoroacetic anhydride (Y=trifluoroacetoxy) and trifluoroacetic esters (Y=C$_1$–C$_4$-alkoxy), with methyl and ethyl trifluoroacetates being very particularly preferred.

The preparation of the 4-trichloromethyl-6-trifluoromethyl-1,3,5-triazines IV is preferably carried out with equimolar amounts of N-trichloroacetamidinoguanidine II and trifluoroacetic acid derivative III; amounts of from 100 to 500 mol %, in particular from 200 to 250 mol %, of trifluoroacetic acid derivative III based on II are preferred.

The reaction is preferably carried out in an inert solvent or diluent at from −40° C. to the boiling point of the solvent, preferably from −20° to 120° C., in particular from −10° to 100° C.

Suitable solvents and diluents are, very generally, hydrocarbons such as hexane, heptane, pinane, octane, nonane, o-, m-, p-cymene, petroleum fractions boiling in the range from 70° to 190° C., cyclohexane, methylcyclohexane, petroleum ether, decalin, naphtha, 2,2,3-trimethylpentane, 2,2,4-trimethylpentane and 2,3,3-trimethylpentane, halohydrocarbons such as dichloromethane, chloroform, tetrachloromethane, 1,1-dichloroethane, 1,2-dichloroethane, 1,1,1-trichloroethane, 1,1,2-trichloroethane, 1,1,2,2-tetrachloroethane, 1,1,1,2-tetrachloroethane, pentachloroethane, 1,2-cis-dichloroethylene, trichloroethylene, tetrachloroethylene, dichloropropane, dichlorobutane, fluorobenzene, chlorobenzene, bromobenzene, iodobenzene, o-, m-, p-difluorobenzene, o-, m-, p-dichlorobenzene, o-, m-, p-dibromobenzene, 1,2,4-trichlorobenzene, o-, m-, p-chlorotoluene, chloronaphthalene and 1,2-dichloronaphthalene, ethers such as diethyl ether, ethyl n-propyl ether, diisopropyl ether, di-n-butyl ether, diisobutyl ether, n-butyl ethyl ether, methyl tert-butyl ether, diisoamyl ether, cyclohexyl methyl ether, ethylene glycol dimethyl ether, anisole, phenetole, tetrahydrofuran, dioxane and β,β'-dichlorodiethyl ether, thioethers such as thioanisole, nitrohydrocarbons such as nitromethane, nitroethane, nitrobenzene, o-nitrotoluene and o-, m-, p-chloronitrobenzene, nitriles such as acetonitrile, butyronitrile, isobutyronitrile, benzonitrile and m-chlorobenzonitrile, esters such as ethyl acetate, ethyl acetoacetate and isobutyl acetate, amides such as formamide, methylformamide, dimethylformamide and diethylformamide, ketones such as acetone and methyl ethyl ketone, and mixtures of the said solvents.

Diethyl ether is the particularly preferred solvent for step (a) using trifluoroacetic anhydride or trifluoroacetyl chloride.

When a trifluoroacetic ester is used for the reaction, it is particularly preferable to employ tetrahydrofuran or the trifluoroacetic ester itself.

The amount of solvent is not critical and is normally from 1 to 5 times the amount of N-trichloroacetamidinoguanidine II.

Special conditions relating to the pressure are unnecessary, and the reaction is generally carried out under atmospheric pressure.

Step (a) can be carried out in the presence of a basic catalyst. The addition of a base is particularly preferred especially when the reaction is carried out with a trifluoroacetic ester. By contrast, when the reaction is carried out with trifluoroacetic anhydride it is particularly preferable for no base to be present.

Examples of suitable bases are alkali metal hydroxides such as sodium and potassium hydroxide, alkaline earth metal hydroxides such as calcium and magnesium hydroxide, alkaline earth metal oxides such as calcium and magnesium oxide, other metal hydroxides such as aluminum hydroxide, alkali metal carbonates such as sodium and potassium carbonate, alkaline earth metal carbonates such as calcium and magnesium carbonate, alkali metal bicarbonates such as sodium and potassium bicarbonate, alkaline earth metal bicarbonates such as magnesium and calcium bicarbonate, alkali metal acetates such as sodium and potassium acetate, alkaline earth metal acetates such as magnesium and calcium acetate, alkali metal or alkaline earth metal alcoholates such as sodium and potassium methanolate, sodium and potassium ethanolate, sodium and potassium n-propanolate, sodium and potassium isopropanolate, sodium and potassium tertbutanolate, magnesium methanolate and magnesium ethanolate, tertiary aliphatic amines such as trimethylamine, triethylamine, tri-n-propylamine, triisopropylamine, tri-n-butylamine, dimethylethylamine, dimethyldodecylamine and dimethyl-tert-butylamine, tertiary cycloaliphatic amines such as 1,8-diazabicyclo[2.2.2]octane and 1,8-diazabicyclo [5.4.0]-7-undecene, tertiary anilines such as N,N-dimethylaniline, N,N-diethylaniline, N-ethyl-N-methylaniline and methyldiphenylamine, and tertiary heterocyclic amines such as 4-dimethylaminopyridine.

The amount of base is normally from 10 to 200 mol % of the amount of N-trichloroacetamidinoguanidine II. Larger amounts are possible but usually do not have further advantages. When the reaction is carried out with a trifluoroacetic ester, equimolar amounts of base and N-trichloroacetamidinoguanidine II are particularly preferred.

In a particularly preferred embodiment, the N-trichloroacetamidinoguanidine II is introduced into a solvent and then the trifluoroacetic ester III is metered in.

Step (a) can be carried out either continuously or batchwise. In the continuous procedure the reactants are preferably passed through a tube reactor.

The reaction mixture is generally worked up by removing the low-boiling components under reduced pressure, neutralizing residual acid and dissolving the inorganic components out by stirring the crude product with water.

The replacement of the trichloromethyl group in the 4-trichloromethyl-6-trifluoromethyl-1,3,5-triazine IV obtained in step (a) by an alkoxy or alkylthio group is carried out in an inert solvent as mentioned for step (a) unless it is advisable to use an excess of the alcohol or thiol V.

The reaction is expediently carried out in the presence of a basic catalyst. Bases suitable for this purpose are alkali metal alcoholates and amines as mentioned above. It is particularly preferred to use the alkali metal alcoholates of the particular alcohol or thiol V.

The amount of solvent is not critical and is normally from 5 to 10 times the amount of 4-trichloromethyl-6-trifluoromethyl-1,3,5-triazine IV unless an excess of alcohol V is used in the absence of solvent.

For complete reaction, the amount of alcohol or thiol of the formula V must be at least equimolar to the amount of 4-trichloromethyl-6-trifluoromethyl-1,3,5triazine IV. If no solvent is used, preferably from 4 to 5 moles of alcohol or thiol V are used per mole of 4-trichloromethyl-6-trifluoromethyl-1,3,5-triazine IV.

The amount of base is generally from 1 to 200 mol % based on the amount of 4-trichloromethyl-6-trifluoromethyl-1,3,5-triazine IV. The amount of base is preferably from 5 to 50 mol % in the case of $C_1$- and $C_2$-alcohols and thiols V and more than 50 mol % in the case of compounds V with 3 or more carbon atoms.

Step (b) is preferably carried out at from 0° C. to the boiling point of the particular solvent, preferably from 20° to 150° C., in particular from 40° to 80° C.

The reaction mixture is worked up in a conventional manner, usually by removing the low-boiling components under reduced pressure after neutralization.

Step (b) can be carried out either continuously or batchwise. When carried out continuously, the reactants are passed, for example, over a fixed bed of an insoluble base, or the reaction is carried out in a solution saturated with product I, with continuous removal of newly formed product.

One variant of the process according to the invention comprises subjecting the product IV of step (a) to step (b) without isolating it from the reaction mixture, in which case acid by-products from (a) can be neutralized by a higher concentration of basic catalyst. This procedure can be modified in such a way that, after step (a), the low-boiling components are removed, and the resulting product is subjected, if required in a different, suitable solvent, to step (b).

The process according to the invention can be used successfully to synthesize all 6-trifluoromethyl-1,3,5-triazines I complying with the definition, especially the compounds in Table 1. The 6-trifluoromethyl-1,3,5-triazines I are valuable intermediates for crop protection agents as are disclosed, for example, in EP-A 111 442 and DE-A 39 09 146.

TABLE 1

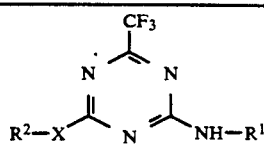

| No. | X | $R^1$ | $R^2$ | m.p. [°C.] |
|---|---|---|---|---|
| 1 | O | H | $CH_3$ | 163–165 |

TABLE 1-continued

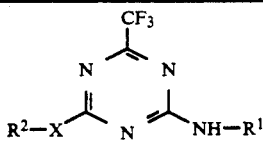

| No. | X | R¹ | R² | m.p. [°C.] |
|---|---|---|---|---|
| 2 | O | H | $C_2H_5$ | 124–128 |
| 3 | O | H | $n-C_3H_7$ | 100–103 |
| 4 | O | H | $i-C_3H_7$ | |
| 5 | O | H | $n-C_4H_9$ | 93–94 |
| 6 | O | H | $i-C_4H_9$ | 102–104 |
| 7 | O | H | $s-C_4H_9$ | |
| 8 | O | H | $t-C_4H_9$ | |
| 9 | O | H | $CH_2CH=CH_2$ | 102–104 |
| 10 | O | H | $E-CH_2CH=CHCH_3$ | |
| 11 | O | H | $CH_2C\equiv CH$ | |
| 12 | O | H | $CH_2C\equiv CCH_3$ | |
| 13 | O | H | Cyclopropyl | |
| 14 | O | H | Cyclobutyl | |
| 15 | O | H | Cyclopentyl | |
| 16 | O | H | Cyclohexyl | |
| 17 | O | $CH_3$ | $CH_3$ | 134–135 |
| 18 | O | $CH_3$ | $C_2H_5$ | |
| 19 | O | $CH_3$ | $n-C_3H_7$ | |
| 20 | O | $CH_3$ | $i-C_3H_7$ | |
| 21 | O | $CH_3$ | $n-C_4H_9$ | |
| 22 | O | $CH_3$ | $i-C_4H_9$ | |
| 23 | O | $CH_3$ | $s-C_4H_9$ | |
| 24 | O | $CH_3$ | $t-C_4H_9$ | |
| 25 | O | $CH_3$ | $CH_2CH=CH_2$ | |
| 26 | O | $CH_3$ | $E-CH_2CH=CHCH_3$ | |
| 27 | O | $CH_3$ | $CH_2C\equiv CH$ | |
| 28 | O | $CH_3$ | $CH_2C\equiv CCH_3$ | |
| 29 | O | $CH_3$ | Cyclopropyl | |
| 30 | O | $CH_3$ | Cyclobutyl | |
| 31 | O | $CH_3$ | Cyclopentyl | |
| 32 | O | $CH_3$ | Cyclohexyl | |
| 33 | O | $C_2H_5$ | $CH_3$ | |
| 34 | O | $C_2H_5$ | $C_2H_5$ | |
| 35 | O | $C_2H_5$ | $n-C_3H_7$ | |
| 36 | O | $C_2H_5$ | $i-C_3H_7$ | |
| 37 | O | $C_2H_5$ | $n-C_4H_9$ | |
| 38 | O | $C_2H_5$ | $i-C_4H_9$ | |
| 39 | O | $C_2H_5$ | $s-C_4H_9$ | |
| 40 | O | $C_2H_5$ | $t-C_4H_9$ | |
| 41 | O | $C_2H_5$ | $CH_2CH=CH_2$ | |
| 42 | O | $C_2H_5$ | $E-CH_2CH=CHCH_3$ | |
| 43 | O | $C_2H_5$ | $CH_2C\equiv CH$ | |
| 44 | O | $C_2H_5$ | $CH_2C\equiv CCH_3$ | |
| 45 | O | $C_2H_5$ | Cyclopropyl | |
| 46 | O | $C_2H_5$ | Cyclobutyl | |
| 47 | O | $C_2H_5$ | Cyclopentyl | |
| 48 | O | $C_2H_5$ | Cyclohexyl | |
| 49 | O | $n-C_3H_7$ | $CH_3$ | |
| 50 | O | $i-C_4H_9$ | $C_2H_5$ | |
| 51 | O | $n-C_3H_7$ | $n-C_3H_7$ | |
| 52 | O | $i-C_4H_9$ | $i-C_3H_7$ | |
| 53 | O | $n-C_3H_7$ | $n-C_4H_9$ | |
| 54 | O | $s-C_4H_9$ | $i-C_4H_9$ | |
| 55 | O | $i-C_3H_7$ | $s-C_4H_9$ | |
| 56 | O | $t-C_4H_9$ | $t-C_4H_9$ | |
| 57 | O | $i-C_3H_7$ | $CH_2CH=CH_2$ | |
| 58 | O | $t-C_4H_9$ | $E-CH_2CH=CHCH_3$ | |
| 59 | O | $i-C_3H_7$ | $CH_2C\equiv CH$ | |
| 60 | O | $s-C_4H_9$ | $CH_2C\equiv CCH_3$ | |
| 61 | O | $i-C_3H_7$ | Cyclopropyl | |
| 62 | O | $i-C_3H_7$ | Cyclobutyl | |
| 63 | O | $i-C_3H_7$ | Cyclopentyl | |
| 64 | O | $t-C_4H_9$ | Cyclohexyl | |
| 65 | S | H | $CH_3$ | |
| 66 | S | H | $C_2H_5$ | |
| 67 | S | H | $n-C_3H_7$ | |
| 68 | S | H | $i-C_3H_7$ | |
| 69 | S | H | $n-C_4H_9$ | |
| 70 | S | H | $i-C_4H_9$ | |
| 71 | S | H | $s-C_4H_9$ | |
| 72 | S | H | $t-C_4H_9$ | |
| 73 | S | H | $CH_2CH=CH_2$ | |
| 74 | S | H | $E-CH_2CH=CHCH_3$ | |

TABLE 1-continued

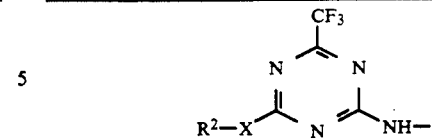

| No. | X | R¹ | R² | m.p. [°C.] |
|---|---|---|---|---|
| 75 | S | H | $CH_2C\equiv CH$ | |
| 76 | S | H | $CH_2C\equiv CCH_3$ | |
| 77 | S | H | Cyclopropyl | |
| 78 | S | H | Cyclobutyl | |
| 79 | S | H | Cyclopentyl | |
| 80 | S | H | Cyclohexyl | |
| 81 | S | $CH_3$ | $CH_3$ | |
| 82 | S | $CH_3$ | $C_2H_5$ | |
| 83 | S | $CH_3$ | $n-C_3H_7$ | |
| 84 | S | $CH_3$ | $i-C_3H_7$ | |
| 85 | S | $CH_3$ | $n-C_4H_9$ | |
| 86 | S | $CH_3$ | $i-C_4H_9$ | |
| 87 | S | $CH_3$ | $s-C_4H_9$ | |
| 88 | S | $CH_3$ | $t-C_4H_9$ | |
| 89 | S | $CH_3$ | $CH_2CH=CH_2$ | |
| 90 | S | $CH_3$ | $E-CH_2CH=CHCH_3$ | |
| 91 | S | $CH_3$ | $CH_2C\equiv CH$ | |
| 92 | S | $CH_3$ | $CH_2C\equiv CCH_3$ | |
| 93 | S | $CH_3$ | Cyclopropyl | |
| 94 | S | $CH_3$ | Cyclobutyl | |
| 95 | S | $CH_3$ | Cyclopentyl | |
| 96 | S | $CH_3$ | Cyclohexyl | |
| 97 | S | $C_2H_5$ | $CH_3$ | |
| 98 | S | $n-C_3H_7$ | $C_2H_7$ | |
| 99 | S | $i-C_4H_9$ | $n-C_3H_7$ | |
| 100 | S | $n-C_3H_7$ | $i-C_3H_7$ | |
| 101 | S | $i-C_4H_9$ | $n-C_4H_9$ | |
| 102 | S | $n-C_3H_7$ | $i-C_4H_9$ | |
| 103 | S | $s-C_4H_9$ | $s-C_4H_9$ | |
| 104 | S | $i-C_3H_7$ | $t-C_4H_9$ | |
| 105 | S | $t-C_4H_9$ | $CH_2CH=CH_2$ | |
| 106 | S | $i-C_3H_7$ | $E-CH_2CH=CHCH_3$ | |
| 107 | S | $t-C_4H_9$ | $CH_2C\equiv CH$ | |
| 108 | S | $i-C_3H_7$ | $CH_2C\equiv CCH_3$ | |
| 109 | S | $s-C_4H_9$ | Cyclopropyl | |
| 110 | S | $i-C_3H_7$ | Cyclobutyl | |
| 111 | S | $i-C_4H_9$ | Cyclopentyl | |
| 112 | S | $i-C_3H_7$ | Cyclohexyl | |

PREPARATION EXAMPLES

Example 1

2-Amino-4-trichloromethyl-6-trifluoromethyl,1,3,5-triazine

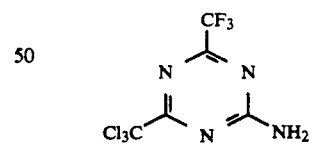

Process variant 1 (without base)

150 g (0.74 mol) of N-trichloroacetamidinoguanidine were added in 3 portions to a vigorously stirred solution of 320 g (1.52 mol) of trifluoroacetic anhydride and 500 ml of diethyl ether at 0° C., with efficient cooling, but adding the last portion without cooling. The mixture was then stirred for 3 hours, the low-boiling fractions were removed at 50° C. under reduced pressure, and 1.5 l of methylene chloride were added to the residue. The organic phase was washed with 3 normal sodium hydroxide solution until neutral and dried over sodium sulfate. Removal of the solvent resulted in a crystalline crude product which was suspended in 200 ml of water for 2 hours. The residue was then separated off and dissolved in methylene chloride. The solution was dried and then the solvent was removed under reduced pressure.

Yield: 85%.

Process variant 2 (with base)

In each case, 0.1 mol of N-trichloroacetamidinoguanidine was reacted with n mol of ethyl trifluoroacetate in the presence of 0.1 mol of a base B at T° C. for t hours. Conventional working up provided the 2-amino-4-trichloromethyl-6-trifluoromethyl-1,3,5-triazine (I) in a yield of Z %.

The details of these experiments are to be found in Table 2:

TABLE 2

| Experiment | n [mol] | Base B | T[°C.] | t[h] | Z |
|---|---|---|---|---|---|
| 1 | 0.5 | 1,4-diazabicyclo[2.2.2]-octane | 62 | 0.7 | 83 |
| 2 | 0.5 | 4-dimethylaminopyridine | 62 | 2 | 84 |
| 3 | 0.5 | 1,8-diazabicyclo[5.4.0]-7-undecene | 62 | 16 | 81 |
| 4 | 0.45 | 30% solution of CH₃ONa in CH₃OH | 0–5 | 0.2 | 95 |

Physical data: melting point 112° to 114° C.; ¹H-NMR (in (CD₃)₂SO; 270 MHz, TMS as standard [ppm]): 9.07 (s, br); 9.02 (s, br); ¹³C-NMR (in (CD₃)₂SO; 67.9 MHz, TMS as standard [ppm]): 173.9 (s); 167.8 (s); 165.1 (q, $^2J_{C-F}=37$ Hz); 118.8 (q, $^1J_{C-F}=277$ Hz); 95.4 (s).

Example 2

2-Amino-4-methoxy-6-trifluoromethyl-1,3,5-triazine

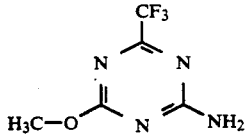

1.8 g of a 30% by weight solution of sodium methanolate in methanol (corresponding to 0.01 mol of sodium methanolate) were added at 22° C. to a solution of 28.8 g (0.1 mol) of 2-amino-4-trichloromethyl-6-trifluoromethyl-1,3,5-triazine in 100 ml of methanol. The pale yellow solution was then refluxed for 30 minutes. The progress of the reaction was followed by thin-layer chromatography on silica gel (mobile phase: diethyl ether/hexane 1:1). After the reaction was complete, 20 ml of water were added, followed by 2 normal hydrochloric acid until the pH was 6–7. After this most of the methanol was removed at 40° C. under reduced pressure, adding 150 ml of water a little at a time so that the product did not agglomerate. To complete precipitation of the product, the resulting mixture was then stirred at 5° C. for 1 hour, after which the product was separated off, washed with a little water and dried at 40° C. under reduced pressure.

Yield: 95%; melting point 163° to 165° C.; ¹H-NMR (in (CD₃)₂SO; 270 MHz, TMS as standard [ppm]): 8.35 (br); 8.17 (br); 8.17 (br); 3.99 (s); ¹³C-NMR (in (CD₃)₂SO; 7.9 MHz, TMS as standard [ppm]): 171.7 (s); 168.9 (s); 165.2 (q, $^2J_{C-F}=36$ Hz); 119.1 (q, $^1J_{C-F}=277$ Hz); 55.1 (s)

Example 3

2-Amino-4-ethoxy-6-trifluoromethyl-1,3,5-triazine

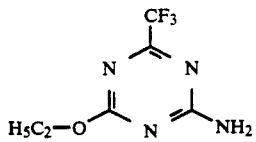

20.0 g (71 mmol) of 2-amino-4-trichloromethyl-6-trifluoromethyl-1,3,5-triazine were added at 22° C. to a solution of 0.48 g (7.1 mmol) of sodium ethanolate in 100 ml of ethanol. The pale yellowish green solution was then refluxed for 30 minutes and, after cooling to 20° C., 20 ml of water were added and the mixture was neutralized with 2 normal hydrochloric acid. After this, most of the solvent was removed at 40° C. under reduced pressure, adding 100 ml of water a little at a time so that the solid did not agglomerate. The product was isolated in a similar manner to Example 2.

Yield: 92%; melting point 124 to 128° C.; ¹H-NMR (in (CD₃)₂SO; 270 MHz, TMS as standard [ppm]): 8.26 (br); 8.14 (br); 4.42 (q, $^3J_{H-H}=7$ Hz); 1.37 (t; $^3J_{H-H}=7$ Hz); ¹³C-NMR (in (CD₃)₂SO; 7.9 MHz, TMS as standard [ppm]): 171.6; 169.0; (q, $^2J_{C-F}=38$ Hz); 118.8 (q, $^1J_{C-F}=277$ Hz); 64.7; 14.2.

Example 4

2-Amino-4-(n-propoxy)-6-trifluoromethyl-1,3,5-triazine

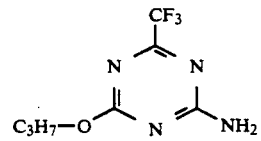

20.0 g (71 mmol) of 2-amino-4-trichloromethyl-6-trifluoromethyl-1,3,5-triazine were added at 22° C. to a solution of 0.58 g (7.1 mmol) of sodium propanolate in 40 ml of propanol. The resulting yellow mixture was then heated at 75° C. for 30 minutes, after which a further 0.58 g (7.1 mmol) of sodium propanolate in 10 ml of propanol was added and the mixture was heated at 75° C. for 10 minutes. The reaction mixture was cooled to 20° C. and then neutralized with 2 normal aqueous hydrochloric acid. After this, most of the solvent was removed under reduced pressure, and the residue was slowly diluted with 40 ml of water. The solid which formed was separated off, washed with 5 ml of water and dried at 40° C. under reduced pressure.

Yield: 93%; melting point 100° to 103° C.; ¹H-NMR (in CDCl₃; 270 MHz, TMS as standard [ppm]): 6.95 (br); 6.02 (br); 4.34 (t, $^3J_{H-H}=7$ Hz); 1.82 (sext; $^3J_{H-H}=7$ Hz), 1.03 (t; $^3J_{H-H}=7$ Hz); ¹³C-NMR (in CDCl₃; 68 MHz, TMS as standard [ppm]): 171.9; 169.1; 166.5 (q, $^2J_{C-F}=37$ Hz); 118.9 (q; $^1J_{C-F}=277$ Hz); 70.4; 22.1; 10.3.

Example 5

2-Amino-4-methoxy-6-trifluoromethyl-1,3,5-triazine

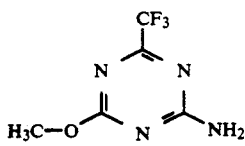

2.7 g (18 mmol) of 1,8-diazabicyclo[5.4.0]-7-undecene were added at 22° C. to a solution of 5 g (18 mmol) of 2-amino-4-trichloromethyl-6-trifluoromethyl-1,3,5-triazine in 25 ml of methanol. The mixture was refluxed for 1 hour and, after cooling to 20° C., made weakly acid (pH=6) with 2 normal aqueous hydrochloric acid. Then most of the solvent was removed under reduced pressure, after which the solid was isolated in a conventional manner.

Yield: 89%; melting point 163° to 165° C.

Example 6

2-Methoxy-4-methylamino-6-trifluoromethyl-1,3,5-triazine

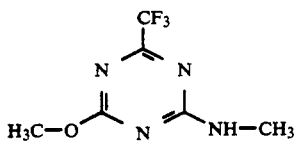

21.8 g of a 30% strength solution of sodium methanolate in methanol (0.12 mol of sodium methanolate) were added dropwise to a solution of 119.4 g (0.40 mol) of 2-methylamino-4-trichloromethyl-6-trifluoromethyl-1,3,5-triazine in 400 ml of methanol. The resulting yellow mixture was then refluxed for 1 hour during which it gradually became cloudy. After addition of a further 7.2 g of the 30% strength solution of sodium methanolate in methanol (0.04 mol of sodium methanolate), the mixture was refluxed for a further 30 minutes and, after cooling to 20° to 25° C., diluted with 150 ml of water and neutralized with 1 normal aqueous hydrochloric acid. The solvent was then removed at 40° C. under reduced pressure, after which the resulting solid was separated off and dried at 40° C. under reduced pressure for 15 hours.

Yield: 93%; melting point 134° to 135° C. (rotamer mixture); $^1$H-NMR (in CDCl$_3$; 270 MHz, TMS as standard [ppm]): 6.51 (br); 3.20 (d) and 6.28 (br); 3.16 (d); $^{13}$C-NMR (in (CDCl$_3$; 67.9 MHz, TMS as standard [ppm]): 75.2 (s); 167.1 (s); 165.7 (q, $^2J_{C-F}=39$ Hz); 118.5 (q, $^1J_{C-F}=278$ Hz); 95.2 (s) and 174.2 (s); 167.1 (s); 166.0 (q; $^2J_{C-F}=39$ Hz); 118.5 (q; $^1J_{C-F}=278$ Hz); 95.2 (s).

Example 7

One-stage synthesis of 2-amino-4-methoxy-6-trifluoromethyl-1,3,5-triazine (cf. Example 5)

A solution of 25.3 g (197 mmol) of methyl trifluoroacetate in 20 ml of methanol was added dropwise at 0° C. to a stirred solution of 20.0 g (98 mmol) of N-trichloroacetamidinoguanidine in 100 ml of methanol, and then a solution of 10.6 g (197 mmol) of sodium methanolate in 70 ml of methanol was added dropwise at 0° to 5° C. After stirring at 0° to 10° C. for a further 5 minutes, thin-layer chromatography [on silica gel; mobile phase: diethyl ether/hexane 1:1] showed quantitative formation of 2-amino-4-trichloromethyl-6-trifluoromethyl-1,3,5-triazine. The reaction mixture was then stirred at 50° C. until this intermediate was no longer detectable (about 30 minutes) and then cooled to 10° C. and 50 ml of water were added. The mixture was neutralized with 10% by weight aqueous hydrochloric acid (pH=6 to 7) and the methanol was removed at 40° C. under reduced pressure, adding 50 ml of water in such a way that the crude product did not agglomerate. To complete precipitation of the product, the mixture was then stirred at 5° C. for 1 hour, after which it was separated off, washed with a little water and dried at 40° C. under reduced pressure.

Yield: 83%; melting point 163°–165° C.

We claim:

1. A process for preparing a 6-trifluoromethyl-1,3,5-triazine of the formula I

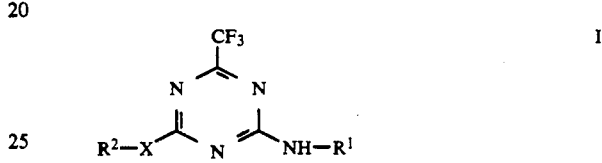

where X is oxygen or sulfur, R$^1$ and R$^2$ are each carbon organic substituents with 1 to 6 carbons and R$^1$ is additionally hydrogen, which comprises (a) reacting an N-trichloroacetamidinoguanidine of the formula II

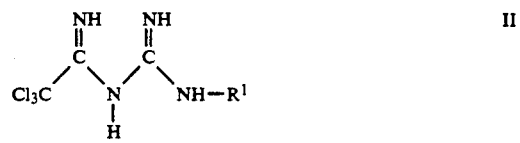

with a trifluoroacetic acid derivative of the formula III

where Y is chlorine, C$_1$–C$_4$-alkoxy or trifluoroacetoxy, in the presence or absence of a base to give a 4-trichloromethyl-6-trifluoromethyl-1,3,5-triazine of the formula IV

and (b) reacting the product IV in the presence of a base with an alcohol or thiol of the formula V

2. A process as claimed in claim 1, wherein a trifluoroacetic acid derivative III where Y is C$_1$–C$_4$-alkoxy is used.

3. A process as claimed in claim 1, wherein a trifluoroacetic acid derivative III where Y is trifluoroacetoxy is used.

4. A process as claimed in claim 1, wherein step (a) is carried out in the presence of a basic catalyst.

5. A process as claimed in claim 1, which is used to prepare a compound I where $R^1$ is hydrogen or $C_1$–$C_4$-alkyl.

6. A process as claimed in claim 1, which is used to prepare a compound I where $R^2$ is $C_1$–$C_4$-alkyl, $C_3$–$C_4$-alkenyl, $C_3$–$C_4$-alkynyl or $C_3$–$C_6$-cycloalkyl.

7. A process as claimed in claim 1, wherein the 4-trichloromethyl-6-trifluoromethyl-,1,3,5-triazine IV is not isolated from the reaction mixture before undergoing step (b).

* * * * *